United States Patent [19]

Imura et al.

[11] Patent Number: 5,124,248
[45] Date of Patent: Jun. 23, 1992

[54] MONOCLONAL ANTIBODY RECOGNIZING GAMMA ATRIAL NATRIURETIC POLYPEPTIDE

[75] Inventors: Hiroo Imura; Kazuwa Nakao, both of Kyoto, Japan

[73] Assignee: Shionogi & Co., Ltd., Osaka, Japan

[21] Appl. No.: 380,597

[22] Filed: Jun. 26, 1989

[30] Foreign Application Priority Data

Jul. 4, 1988 [JP] Japan .................. 63-166641

[51] Int. Cl.⁵ .......................... C12Q 33/53
[52] U.S. Cl. .................. 435/7.1; 435/240.27; 435/7.92; 435/7.93; 435/7.95; 435/70.21
[58] Field of Search ............ 530/387; 435/5, 7.1, 435/70.21, 240.27, 7.92, 7.93, 7.95; 436/515, 518

[56] References Cited

FOREIGN PATENT DOCUMENTS 0195331 9/1986 European Pat. Off. .
0306309 3/1989 European Pat. Off. .

OTHER PUBLICATIONS

Itoh et al., "Hypertension", vol. 11(2), Suppl. I., pp. 52-56 (Feb. 1988).

Primary Examiner—Christine Nucker
Assistant Examiner—Jeffrey Stucker
Attorney, Agent, or Firm—Wenderoth, Lind & Ponack

[57] ABSTRACT

A monoclonal antibody which recognizes the N-terminal of gamma-atrial natriuretic polypeptide (γ-ANP). A hybridoma producing said monoclonal antibody and a process for immunoassay of γ-ANP are also provided.

7 Claims, 3 Drawing Sheets

Fig. 1

Asn-Pro-Met-Tyr-Asn-Ala-Val-Ser-Asn-Ala-Asp-Leu-Met-Asp-Phe-Lys-Asn-Leu-Leu-Asp-
                                        10                                      20

His-Leu-Glu-Glu-Lys-Met-Pro-Leu-Glu-Asp-Glu-Val-Val-Pro-Pro-Gln-Val-Leu-Ser-Glu-
                    30                                      40

Pro-Asn-Glu-Glu-Ala-Gly-Ala-Ala-Leu-Ser-Pro-Leu-Pro-Glu-Val-Pro-Pro-Trp-Thr-Gly-
                    50                                      60

Glu-Val-Ser-Pro-Ala-Gln-Arg-Asp-Gly-Gly-Ala-Leu-Gly-Arg-Gly-Pro-Trp-Asp-Ser-Ser-
                    70                                      80

Asp-Arg-Ser-Ala-Leu-Leu-Lys-Ser-Lys-Leu-Arg-Ala-Leu-Leu-Thr-Ala-Pro-Arg-Ser-Leu-
                    90                                      100

Arg-Arg-Ser-Ser-Cys-Phe-Gly-Gly-Gly-Arg-Met-Asp-Arg-Ile-Gly-Ala-Gln-Ser-Gly-Leu-Gly-
                    110                                     120
             |
             S
             |
             S
             |
Cys-Asn-Ser-Phe-Arg-Tyr

MONOCLONAL ANTIBODY RECOGNIZING GAMMA ATRIAL NATRIURETIC POLYPEPTIDE

The present invention relates to a monoclonal antibody which recognizes the N-terminal of gamma atrial natriuretic polypeptide (hereinafter referred to as γ-ANP), a hybridoma which produces the monoclonal antibody, and a method for immunoassay of γ-ANP with the use of the monoclonal antibody.

ANP is a polypeptide contained in granules produced by atrial myocyte, and exerts a natriuretic action as well as a strong diuretic action. Since de Bold, A. J. et al. discovered strong natriuretic activity, diuretic activity and hypotensive activity in atrial extracts (Life Sci. 28, 89–94, 1981), a series of polypeptides called atrial natriuretic polypeptide (ANP) as a whole has been isolated from human and rat atrial tissues, and it has been suggested that the polypeptides are associated with the homeostasis of body fluid and the control of blood pressure (Kangawa, K. et al, Biochem. Biophys. Res. Commun., 118, 131–139, 1984).

Such polypeptides are found not only in humans but also in rats, and called hANP and rANP respectively. The hANP and rANP are each subclassified into three types, namely, α, β, and γ. In this text, human ANP of γ-type and rat ANP of γ-type are abbreviated as γ-hANP and γ-rANP respectively. When it is not necessary to specify the source or subclass of ANP, it is simply referred to as "ANP".

α-hANP consists of 28 amino acid residues. Cys[7], i.e., Cys at the 7th position from the N-terminal, forms a disulfide linkage with Cys[23], i.e., Cys at the 23rd position, and therefore the peptide sequence between Cys[7] and Cys[23] forms a ring structure (Biochem. Biophys. Res. Commun., 118, 131–139, 1984). α-hANP is different from α-rANP in that the amino acid residue at the 12th position from the N-terminal is Met in the former, while it is Ile in the latter (Biochem. Biophys. Res. Commun., 117, 839–865, 1983). β-hANP is an antiparallel dimer of α-hANP (Japanese Patent Unexamined Publication No. 184098/1985).

γ-hANP consists of 126 amino acid residues (see FIG. 1 of the accompanying drawings), and its 99–126 amino acid sequence on the C-terminal exactly corresponds to α-hANP (Nature, 313 397, 1985).

With the use of polyclonal rabbit antiserum against α-ANP [17-28], a radioimmunoassay (RIA) for measuring ANP has been established, which detects both α-hANP and α-rANP (Nakao, K. et al, Biochem. Biophys. Res. Commun., 124, 815–821, 1984), and it has been shown that the α-ANP circulates through the body as a hormone after the secretion from the heart (Sugawara, A. et al, Hypertension 8 (Suppl I), I-151-155, 1986).

On the other hand, studies by RIA and chromatographic analyses revealed that ANP is also present in the central nervous system (Morii, N. et al, Biochem. Biophys. Res., Commun., 127, 413–419, 1985), and that the major molecules of ANP in the brain and spinal cord of rats are α-rANP [4-28] and α-rANP [5-28] (Shiono, S. et al, Biochem. Biophys. Res. Commun., 135, 728–734, 1986; Morii, N. et al, ibid. 145, 196–203, 1987). It has also been shown that ANP in the brain and spinal cord functions as a neuropeptide, while ANP in the circulating blood functions as a hormone (Nakao, N. et al, Can. J. Physiol. Pharmacol. 65, 1756–1761, 1987).

The afore-mentioned polyclonal rabbit antiserum against α-ANP can not distinguish ANP in the circulating blood from ANP in the brain and spinal cord, but it has been used in various ways. For instance, the antiserum was used in immunohistochemical studies (Kawata, M. et al, Neuroscience 16, 521–546, 1985). In addition, the antiserum was injected into the cerebral ventricle of rat to neutralize the action of endogenous ANP in the brain, thereby water intake was enhanced (Katsuura, G. et al, European J. Pharmacol. 121, 285–287, 1986).

Thus, polyclonal antibody to ANP contained in the antiserum are useful in various aspects. However, the antiserum has unavoidable disadvantages in that it has short supply, it contains various antibodies recognizing a variety of epitopes and it contains unnecessary antibodies against antigens other than ANP.

For the above reasons, there has been an eager demand for monoclonal antibody against ANP, and several monoclonal antibodies having various sorts of specificities have recently been reported (Joh, A. et al, Life Sci. 38, 1991–1997, 1986; Milne, R. et al, Mol. Immunol. 24, 127–132, 1987; Glembotski, C. C. et al, Endocrinology 121, 843–852, 1987; Naomi, S. et al, Hybridoma 6, 433–440, 1987; Stasch, J. P. et al, European J. Pharmacol. 129, 165–168, 1986). The inventors of the present invention have also established monoclonal antibodies KY-ANP-I and KY-ANP-II, both of which recognize α-ANP (Japanese Patent Application Serial Nos. 218662/1987 and 47280/1983).

On the other hand, various radioimmunoassays for ANP which utilize antiserum have already been established (Science 228, 323–325, 1985; Nature 314, 264–266, 1985; Biochem. Biophys. Res. Commun., 124, 815–821, 1984; ibid. 124, 663–668, 1984; ibid. 125, 315–323, 1984). It is reported in one of these literatures that antiserum CR-3 was found to recognize C-terminal fragment [17–28] of ANP according to such immunoassay. In addition, radioimmunoassay of γ-ANP utilizing antiserum has been reported (Hypertension, vol.11 No. 2, I-52-56, 1988). Immunohistochemical and neutralizing tests utilizing monoclonal antibodies against ANP are also known.

As stated above, remarkable development has recently been made in the field of ANP-associated science. However, monoclonal antibody capable of specifically recognizing γ-ANP and more efficient immunoassay of γ-ANP utilizing such monoclonal antibody have not been established yet.

The present invention provides a novel monoclonal antibody which specifically recognizes N-terminal sequence of γ-ANP and shows high affinity to γ-ANP. In addition, it provides a highly sensitive method of measuring γ-ANP by the use of the antibody.

The monoclonal antibody of the invention recognizes mainly 25 amino acid residues of from the first amino acid residue to the 25th amino acid residue on the N-terminal of γ-ANP. The segment consisting of such amino acid residues is described as γ-ANP[1-25] in this text for the purpose of simplicity. The monoclonal antibody of the invention recognizes both γ-hANP and γ-rANP. The antibody allows highly sensitive measurement of γ-ANP in RIA. Furthermore, when the antibody is used in combination with any known antibody recognizing α-ANP, such as CR-3, 11A-A11, KY-ANP-I, or KY-ANP-II, it is possible to conduct sandwich enzyme immunoassay (EIA) with very high sensitivity, because γ-ANP[99-126] is identical with α-ANP[1-28], at least as far as human ANP is concerned.

DETAILED DESCRIPTION

After having made strenuous studies for the purpose of creating monoclonal antibodies, which exhibit high affinity to γ-hANP and specifically recognize the N-terminal fragment of γ-hANP, the inventors have succeeded in obtaining monoclonal antibodies which recognize the N-terminal of γ-hANP, and establishing a highly sensitive method of measuring γ-hANP by the use of the antibodies. The process for preparing said monoclonal antibodies and the process for measuring γ-hANP are detailed below.

(1) Preparation of a hybridoma producing a monoclonal antibody

As previously mentioned, γ-hANP[99-126] exactly corresponds to α-hANP[1-28]. Accordingly, a fragment consisting of all or part of γ-hANP[1-98] is employed as an antigen for preparing an antibody specific to γ-hANP. The fragment is conjugated with any other protein of higher molecular weight, such as bovine serum albumin or bovine thyroglobulin, when it is used as an immunogen. The conjugate thus obtained is emulsified in a suitable adjuvant, such as Freund's complete adjuvant, and then is used to immunize mice.

Immunization is performed by repeatedly inoculating the above emulsion into mice at intervals of several weeks intraperitoneally, subcutaneously or intravenously. Three to seven days after the last immunization, the spleen is taken out, which is used as a source providing antibody-producing cells. On the other hand, myeloma cells having a suitable marker such as hypoxanthine-guanine-phosphoribosyl transferase-deficiency (HGPRT$^-$) or thymidine kinase deficiency (TK$^-$) are prepared. The antibody-producing cells and the myeloma cells are then fused to prepare a hybridoma.

As a culture medium for the hybridoma growth, there may be employed such media as Eagle's MEM, Dulbecco's modified medium, or RPMI-1640, with the addition of about 15% fetal calf serum (FCS), although the medium is not limited thereto.

First, the myeloma cells and the spleen cells are mixed at the ratio of about 1:10 in the presence of a fusing agent. As the fusing agent, 50% polyethylene glycol (PEG) is generally employed because of its high fusing efficiency. Fused cells are selected by HAT selection method. The hybridomas contained in the culture supernatant are screened according to conventional methods such as membrane fluorescence antibody technique, enzyme linked immunosorbent assay (ELISA method), immunological tissue staining method, and RIA, to select aimed hybridomas capable of secreting desired immunoglobulin. For the purpose of securing the homogeneity of the selected hybridomas, re-cloning is conducted as follows: normal spleen cells are placed as a feeder layer in a 96-well microplate and the selected hybridomas are placed thereon at a rate not exceeding one cell per well, and screening is performed again on cultured clones. Homogeneous hybridomas are obtained by repeating such sub-cloning process.

(2) Production of monoclonal antibody

The hybridomas obtained above are cultured in vitro or in vivo to prepare a monoclonal antibody of the present invention. When the culture is conducted in vitro, conventional media such as mentioned above may be used with addition of FCS. After culturing in the medium for 3 to 5 days, the monoclonal antibody is obtained from the culture supernatant. When the culture is conducted in vivo, the hybridoma is inoculated into the abdominal cavity of a mammal. One to two weeks after that, ascites fluid is collected, from which monoclonal antibody is obtained. As compared with in vitro culture, in vivo culture produces a far larger quantity of antibody, and therefore, is preferred.

The monoclonal antibody obtained from culture supernatant or ascites fluid is purified by known methods, such as ammonium sulfate fractionation, adsorption to Protein A column and DEAE Sepharose column chromatography, or a combination thereof.

The inventors have obtained a monoclonal antibody to γ-ANP in accordance with the process as mentioned above, which was designated as KY-ANP-III, and have examined its characteristics. The monoclonal antibody showed high affinity with γ-hANP ($Ka = 5.3 \times 10^9 M^{-1}$).

The antibody exhibited strong cross-reactivity with γ-hANP[1-25] and γ-hANP[1-72]. However, only a weak cross-reactivity was observed with γ-hANP[1-10] and γ-hANP[17-25]. This indicates that the first 25 amino acid residues of the N-terminal of γ-hANP is most important for recognition by the antibody. The antibody also showed cross-reactivity with γ-rANP.

The hybridoma KY-ANP-III which produces the monoclonal antibody, KY-ANP-III, of the present invention has been deposited with the Fermentation Research Institute, Agency of the Industrial Science & Technology, Higashi 1-1-3, Tsukuba City, Ibaraki Prefecture, Japan, since May 18, 1988, under the name of Mouse hybridoma KY-ANP-III, Bikoken Joki No. 1887 (FERM BP-1887), in compliance with the Budapest Treaty.

As an immunoassay of γ-ANP using the monoclonal antibody, KY-ANP-III, of the present invention, RIA which employs a single antibody, or sandwich EIA may be mentioned. As regards RIA, a competitive method may be mentioned in which, as shown in the Example hereinafter described, a sample to be tested or a standard γ-ANP and a predetermined amount of isotope-labeled γ-ANP are allowed to competitively bind to the antibody, and the radioactivity bound to the antibody is measured.

Sandwich EIA is conducted employing the antibody KY-ANP-III in combination with other antibody, for instance, the afore-mentioned antiserum CR-3, KY-ANP-I, and KY-ANP-II, which all react with γ-ANP[99-126] in such a manner as mentioned below.

As a solid phase for immobilizing the antibody, there may be used such carriers as glass or plastic beads or balls, tubes and plates, which are commercially available and are generally used in immunoassay as a carrier for an antigen-antibody reaction. An antibody recognizing α-ANP or γ-ANP is adsorbed to any of these carriers. The adsorption is usually performed by allowing the antibody to contact with the carrier overnight in a phosphate buffer at pH 6-10, preferably at around neutral pH, at room temperature. The carrier on which the antibody has been adsorbed is stored in a cold place in the presence of an antiseptic agent such as sodium azide.

Both monoclonal antibody and polyclonal antibody can be used in the above procedure. Separation and purification of the antibody to be employed in the above procedure can be conducted in the following manner.

Ascites or antiserum containing the antibody is fractionated with sodium sulfate, and then passed through a DEAE-cellulose column, whereby IgG is obtained. The IgG thus obtained is digested with pepsin to make F(ab')₂ fragment, which is then reduced with 2-mercaptoethylamine to obtain anti-α-ANP Fab' or anti-γ-ANP Fab'. Preparation of Fab' from IgG is detailed in J. Immunoassay, 4, 209–327 (1983), and the same procedure may be used in the present invention.

As an enzyme to be employed for the purpose of labelling the antibody, there may be used alkaline phosphatase, β-D-galactosidase, peroxidase, glucose oxidase, etc. In the present invention, however, it is particularly preferable to use horseradish peroxidase. As a bridging agent, which is used to conjugate the enzyme with the antibody, there may be used N,N'-α-phenylenedimaleimide, N-succinimide 4-(N-maleimidomethyl)cyclohexanoate, N-succinimide 6-maleimidohexanoate, N-succinimide 3-(2-pyridyldithio)propionate, 4,4'-dithiopyridine, and other known agents. The reaction of the bridging agent with the enzyme and the antibody is performed in accordance with conventional methods with necessary modification depending on the nature of particular bridging agent.

As will be understood from the above, the fragment of the antibody, such as Fab', Fab, and F(ab')₂, can be used rather than the antibody per se. Furthermore, enzymelabeled antibody can be polyclonal or monoclonal antibody. The purification of the enzyme-labeled antibody obtained by the use of the above-mentioned bridging agent by affinity chromatography provides a more highly sensitive immunoassay system.

The purified enzyme-labeled antibody is stored in a cold and dark place with addition of a stabilizer such as thimerosal or glycerin, or after being lyophilized.

In the preparation of the afore-mentioned reagents for immunoassay, either an antibody recognizing N-terminal of γ-ANP is immobilized where an antibody recognizing α-ANP is enzyme-labeled, or an antibody recognizing α-ANP is immobilized where an antibody recognizing γ-ANP is enzyme-labeled. Since immobilization of an antibody usually requires a large quantity of antibody, the immobilization of a monoclonal antibody, which can be obtained steadily in a large quantity, is preferred. However, a polyclonal antibody prepared from antiserum can also be used without any inconvenience.

An antibody to be enzyme-labeled can also be either a monoclonal antibody or a polyclonal antibody, provided that the antibody recognizes a site different from that recognized by the immobilized antibody. For example, KY-ANP-III of the present invention can be used as an immobilized antibody, while the above-mentioned antiserum CR-3, KY-ANP-I, or KY-ANP-II can be used as an enzymelabeled antibody, and vice versa.

In the accompanying drawings:

FIG. 1 shows an amino acid sequence of γ-hANP.

Figure 3:
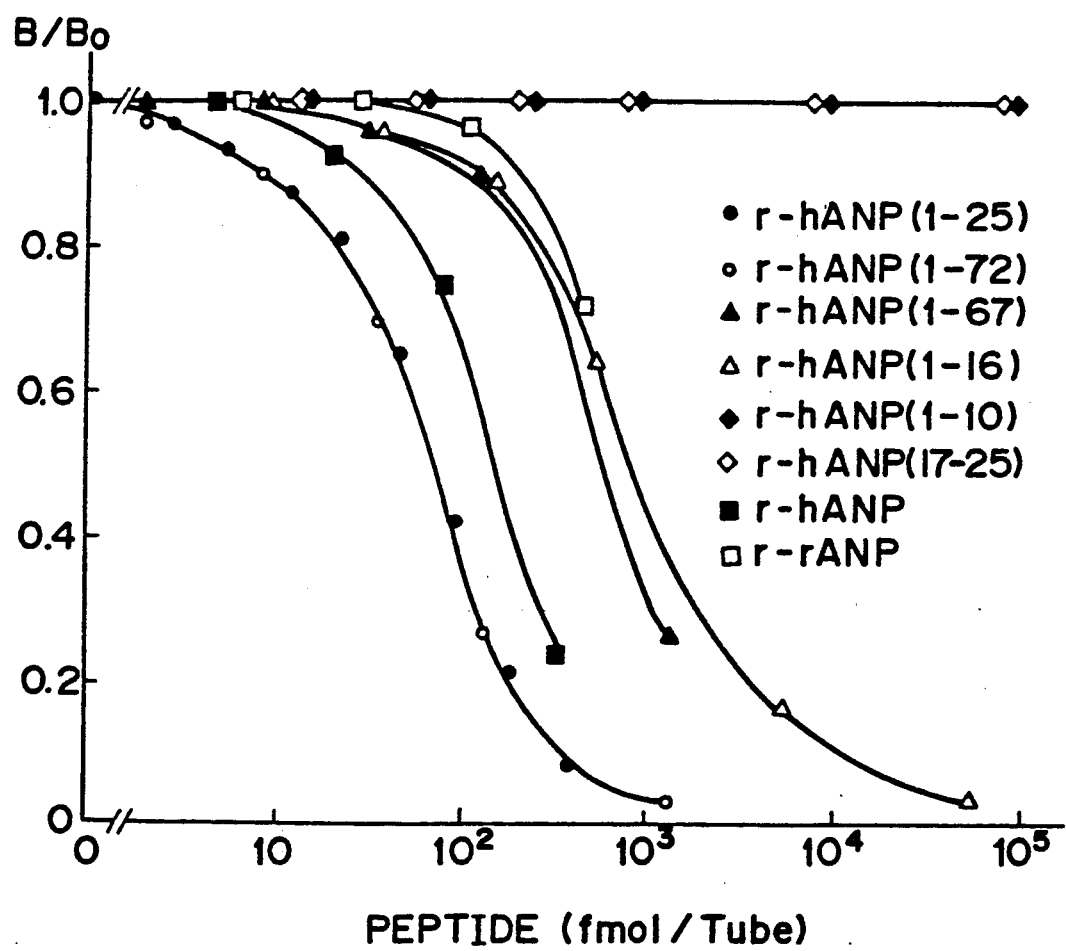

FIG. 3 shows a typical standard curve of γ-hANP in RIA wherein KY-ANP-III is employed, and cross reaction curves of related peptides. [$^{125}$I]γ-hANP[1-25] and standard γ-hANP or related peptides in various concentrations were incubated with KY-ANP-III for 24 hr. at 4° C. The symbols employed in FIG. 3 have the following meanings: ..... γ-hANP[1-25], ○ ..... γ-hANP[1-72], ..... γ-hANP[1-67], △ ..... γ-hANP[1-16], ..... γ-hANP[1-10]. ..... γ-hANP[17-25], . .... γ-hANP, and □ ..... γ-ANP.

The following Example further illustrates and describes the invention disclosed herein. The invention is not limited in scope of the following Example.

EXAMPLE

Preparation of hybridoma

Synthetic γ-hANP[1-25] (5.0 mg) and bovine thyroglobulin (10 mg) were dissolved in 1.6 ml of distilled water. To this solution was added dropwise a solution of 20 mg of 1-ethyl-3-(3-dimethylaminopropyl)carbodiimide in 0.2 ml of distilled water over a period of 10 min. at temperature of 4° C., after which the mixture was stirred at 0° C. for 4 hr. under nitrogen atmosphere. The mixture was then dialyzed 4 times against 1.0 l of distilled water over a period of 3 days. The dialyzate was divided into 5 portions, which were stored at −20° C. (See Biochem. Biophys. Res. Commun., 124, 815–821, 1984).

To each of the stored solutions (each containing 300 μg of γ-hANP[1-25]) was added distilled water to make 1.2 ml, which was then suspended in 1.2 ml of Freund's complete adjuvant. About 2 ml portion was injected intraperitoneally and subcutaneously into 10 BALB/c female mice (200 μl per animal). The animals were then subcutaneously injected seven times with 7.5-30 μg per animal of γ-hANP[1-25] suspended in complete adjuvant with about 4-week interval. Six days after the last immunization with intravenous injection of 30 μg of γ-hANP[1-25], the spleens of the mice were taken out, which were used for cell fusion.

The spleen cells obtained above and myeloma cells X63-Ag8.653 were mixed (1:10) in Dulbecco's medium (DMEM), and the mixture was centrifuged at 1500 rpm for 5 min. at 4° C. The pellets obtained were loosened by warming at 37° C., and then 1 ml of 50% PEG4000 (PEG 1 g/DMEM 1 ml) was added dropwise at 37° C. over a period of 1 min. The mixture was allowed to stand for 2 min. at 37° C., after which it was diluted by dropwise addition of 10 ml of DMEM at 37° C. over a period of 5 min. The mixture was then washed by centrifugation at 4° C. with DMEM containing 15% FCS.

After the cell fusion as mentioned above, the resultant hybridomas were selected in HAT medium containing 15% fetal calf serum. During the culture of the hybridomas, the antibody production in the culture medium was examined periodically by RIA by the use of [$^{125}$I]γ-hANP[1-25]. Growth of hybridomas was observed in almost all wells, 0.8% (3 wells) of which produced antibodies. Cells producing antibodies were cloned twice by the limiting dilution method with the use of mouse thymus cells as a feeder. A clone which produces an antibody having the strongest reactivity, i.e., KY-ANP-III, was established. In order to study the properties of KY-ANP-III, the clone was further cultivated.

Preparation of monoclonal antibody

BALB/c mice were pretreated by intraperitoneally injecting 0.5 ml/animal of pristane twice at intervals of 1 to 2 weeks. To each of the mice was intraperitoneally injected 5×10⁶ cells of hybridoma KY-ANP-III suspended in 200 μl of DMEM. Ascites taken from the mice was purified by means of Protein A-Sepharose CL-4B column to obtain monoclonal antibody KY-ANP-III.

Properties of monoclonal antibody

The isotype of the monoclonal antibody obtained above was determined by Ouchterlony's method (Mouse Monoclonal Typing Kit, Miles). The affinity constant was determined by Scatchard method by means of the RIA to be mentioned later. The specificity of the antibody was analyzed by searching the cross reactivity with various ANP-related peptides by RIA.

Figure 2:
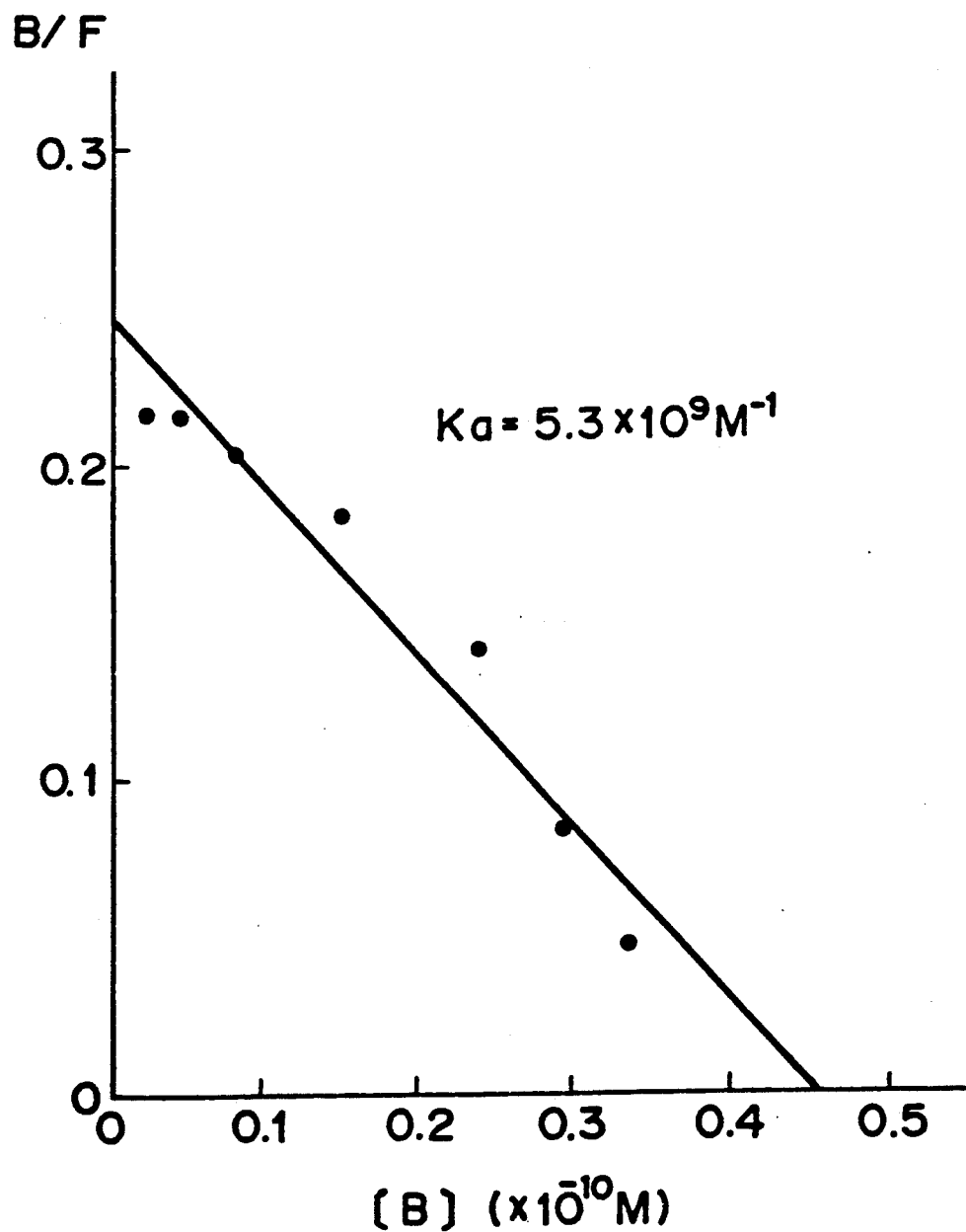
FIG. 2 shows Scatchard plot of the binding between [$^{125}$I]γ-hANP[1-25] and monoclonal antibody KY-ANP-III. Ascites containing KY-ANP-III was incubated with [$^{125}$I]γ-hANP[1-25] (12-800 pM, 500 μl/tube) for 48 hr. at 4° C., and specific binding was measured after separation with dextran-coated charcoal.

The monoclonal antibody obtained was determined to belong to IgG$_1$ subclass by Ouchterlony's method. Affinity constant, measured by Scatchard method, showed a high affinity, with Ka value against γ-hANP[1-25] being $5.3 \times 10^9 \, M^{-1}$ (See FIG. 2).

RIA

The RIA with the use of monoclonal antibody was performed in accordance with the method described in Hypertension, Vol 11, No. 2, I-52-56 (1988), which involves the use of polyclonal antiserum.

The reagents employed were always dissolved in 0.05 M phosphate buffer solution (pH 7.4) containing 0.1% gelatin (Merck), 1 mM Na$_2$EDTA, 0.2 mM cystine, 0.1% Triton X-100, and 0.01% merthiolate.

A mixture of 100 μl of diluted (1:10$^5$) solution of ascites containing KY-ANP-III, 100 μl of a sample or diluted solution of standard γ-ANP, 200 μl of the above-mentioned buffer, and 100 μl of [$^{125}$I]γ-hANP[1-25] (about 10,000 cpm) was allowed to react at 4° C. for 48 hr. The reaction mixture was then added and mixed with 1 ml of dextran-coated charcoal, and allowed to react at 4° C. for 15 min. The reaction mixture was then centrifuged at 4° C. for 30 min. at 3000 rpm, and the radioactivity of the supernatant was measured by a γ counter, thereby the antibody titer of the diluted solution of the sample was obtained. The specific activity of [$^{125}$I]γ-hANP[1-25] was 570 μCi/μg. When the mouse ascites was used after being diluted to $1:5 \times 10^5$, the binding rate with a tracer was about 25%.

The above-mentioned $^{125}$I-γ-hANP[1-25] was prepared by the chloramine T method. That is to say, γ-hANP[1-25] (1 μg) was mixed with Na$^{125}$I (1 mCi), to which was added 10 μl of chloramine T (5.25 mg/ml). Ten seconds after that, 20 μl of sodium pyrosulfite (4.5 mg/ml) was added. To the mixture was further added 1 ml of 2% gelatin and then the resulting $^{125}$I-γ-hANP was purified with Sep-Pak C18 (Waters Co., Ltd.).

The standard curve of γ-hANP determined in RIA with the use of the monoclonal antibody of the present invention, and the cross reactivity with related peptides are shown in FIG. 3.

Since KY-ANP-III of the present invention recognizes γ-rANP as well as γ-hANP, the antibody is suitable for the measurement not only of human ANP but also of ANP of various experimental animals such as rats and mice. KY-ANP-III can be employed together with other known antibodies to ANP in order to determine γ-hANP with high sensitivity. The establishment of the method of measuring γ-hANP by the use of the monoclonal antibody of the present invention has enabled us to easily and accurately diagnose various diseases which are accompanied by abnormality in the balance of body fluid, such as heart diseases, kidney diseases, hypertension (essential and secondary), edematous diseases (cirrhosis, nephrosis, cataplectic edema, etc.), and dehydration, and to follow up the results of treatments.

What we claim is:

1. A monoclonal antibody which recognizes the N-terminal of γ-ANP.

2. A monoclonal antibody of claim 1 which recognizes γ-hANP(1-25).

3. A monoclonal antibody of claim 2 which is monoclonal antibody KY-ANP-III.

4. A hybridoma which produces a monoclonal antibody of claim 1.

5. A hybridoma of claim 4 which is hybridoma KY-ANP-III.

6. A method of quantitatively or qualitatively determining the presence of γ-ANP in a biological sample by immunoassay which comprises:

contacting a monoclonal antibody which recognizes the N-terminal of γ-ANP so as to allow said γ-ANP in the sample and labeled γ-ANP to competitively bind to the antibody and measuring the amount of the labeled γ-ANP bound to the antibody.

7. A method of quantitatively or qualitatively determining the presence of γ-ANP in a biological sample by immunoassay which comprises:

a) contacting the sample with a monoclonal antibody which recognized the N-terminal of γ-ANP and an additional antibody recognizing C-terminal of γ-ANP, concurrently or successively, so as to allow said γ-ANP in the sample to bind both of said monoclonal antibody and said additional antibody and b) measuring the amount of γ-ANP bound to both of the antibodies.

* * * * *